United States Patent [19]

Kayama et al.

[11] Patent Number: 5,268,493

[45] Date of Patent: Dec. 7, 1993

[54] METHOD OF PRODUCING OLEFIN OXIDE

[75] Inventors: Ryuichi Kayama; Hiroshi Igarashi; Toshio Suzuki, all of Koriyama, Japan

[73] Assignee: Nippon Peroxide Co., Ltd., Tokyo, Japan

[21] Appl. No.: 985,573

[22] Filed: Dec. 3, 1992

Related U.S. Application Data

[63] Continuation-in-part of Ser. No. 789,042, Nov. 7, 1991, abandoned.

[30] Foreign Application Priority Data

Nov. 13, 1990 [JP] Japan .................................. 2-304063
Sep. 19, 1991 [JP] Japan .................................. 3-266898

[51] Int. Cl.⁵ .................... C07D 301/16; C07D 303/04
[52] U.S. Cl. ...................... 549/526; 568/860; 568/867
[58] Field of Search .......................................... 549/526

[56] References Cited

U.S. PATENT DOCUMENTS 3,065,245  11/1962  Latourette et al. ................. 549/526
3,130,207  4/1964   Greenspan et al. ................. 549/526
3,404,163  10/1968  Budde et al. ....................... 549/526
4,115,411  9/1978   Dieckelmann et al. ............. 549/526

FOREIGN PATENT DOCUMENTS 55387    7/1982  European Pat. Off. ............ 549/526
3002785  5/1981  Fed. Rep. of Germany ...... 549/526
811852   4/1959  United Kingdom ................ 549/526

OTHER PUBLICATIONS

Websters Third New International Dictionary, unabridged, pp. 54 and 86 (1961).

Primary Examiner—Joseph E. Evans
Attorney, Agent, or Firm—McAulay, Fisher, Nissen, Goldberg & Kiel

[57]    ABSTRACT

An α-olefin oxide is produced with an enhanced reaction selectivity by a method in which an α-olefin having 6 to 30 carbon atoms is epoxidized in an aqueous solution containing hydrogen peroxide, acetic acid, an acid catalyst, for example, sulfuric acid, and a side reaction-inhibiting agent consisting of a water-soluble neutral salt, for example, sodium sulfate, in an amount of 2 to 30% based on the total weight of the aqueous solution, by an in-situ method, while maintaining the pH of the aqueous solution at a level of 0 to 1, and the resultant reaction product is collected.

10 Claims, No Drawings

METHOD OF PRODUCING OLEFIN OXIDE

CROSS REFERENCE TO RELATED APPLICATION

This application is a continuation-in-part of our application Ser. No. 07/789,042, filed on Nov. 7, 1991, now abandoned.

BACKGROUND OF THE INVENTION

1. Field of the Invention

The present invention relates to a method of producing an olefin oxide. More particularly, the present invention relates to a method of producing an α-olefin oxide, with an excellent selectivity.

The α-olefin oxides are industrial materials very useful for various surfactants and polymer-modifying agents.

2. Description of the Related Arts

It is well known that olefin compounds can be converted to corresponding epoxide compounds by a reaction with organic peracid, and in a well known method, the organic peracid is selected from perbenzoic acid and perphthalic acid. In the industrial production of the olefin oxide, however, this method is disadvantageous in that the specific peracid must be synthesized from a corresponding starting acid, and after the oxidation reaction, the resultant acid compound must be recovered by an expensive process.

Also, it is known from D. Swern et al., J. Am. Chem. Soc., 68, 1504 (1964) that α-olefin oxide is synthesized by using a solution of peracetic acid in acetic acid.

In the industrial production of the α-olefin oxide, this method is disadvantageous in that, in the preparation of the peracetic acid solution, a very high concentration of 90% or more of hydrogen peroxide must be employed, and since the oxidation reaction is carried out in a homogeneous reaction system, the resultant α-olefin epoxide must be extracted by adding a large amount of water to the resultant reaction mixture.

To remove the above-mentioned disadvantages, a new method is known in which an olefin is epoxidized with an oxidant mixture of hydrogen peroxide with a carboxylic acid, for example, acetic acid, in the presence of an acid catalyst, for example, a mineral acid, while generating an organic peracid, for example, peracetic acid, from the hydrogen peroxide and carboxylic acid. This method is referred to as an in-situ method, and is now most widely used as the epoxidizing method.

This in-situ method for the production of olefin oxide is advantageous in that the starting olefin can be satisfactorily epoxidized by using the carboxylic acid, for example, acetic acid, in a relatively small amount of about 50 molar% based on the molar amount of the starting olefin, and this epoxidation can be easily effected in a simple reactor. Therefore, this in-situ method is advantageously utilized to epoxidize an unsaturated compound having a di-substituted double bond, for example, a vegetable oil.

Nevertheless, α-olefin, which is a monosubstituted olefin, exhibits a low reactivity. For example, in D. Swern, "Organic Peroxides", Vol. 1 (1970) Wiley-Interscience, it is mentioned that an olefin having one alkyl substituent, namely an α-olefin, exhibits a reactivity corresponding to about 1/22.5 of that of an olefin having two alkyl substituents.

Also, this in-situ method is disadvantageous in that undesirable side reactions, for example, a cleavage reaction of the epoxy ring structure of the resultant olefin epoxide, occur.

To prevent the undesirable side reactions caused by the use of the in-situ method, usually an organic solvent is added to the reaction mixture.

For example, Japanese Unexamined Patent Publication No. 57-145,866 discloses the employment of benzene as an organic solvent; German Patent No. 1,568,016 teaches the use of benzene or toluene; and Japanese Unexamined Patent Publication No. 51-36,448 provides the use of a chlorine-containing organic solvent, for example, chloroform.

Nevertheless, the use of the above-mentioned organic solvents is dangerous, in that benzene is a harmful substance specified by the Labor Safety and Hygiene Law and must be carefully handled. Toluene is also a harmful substance in that it is easily charged with static electricity, and thus there are many reports of fires due to a self-combustion of toluene. Especially, in the epoxidation of the α-olefin with hydrogen peroxide in the presence of toluene, a large amount of heat is generated and oxygen gas is also produced, and thus the use of toluene causes the α-olefin epoxidizing reaction to be very dangerous in that fires often occur.

Further, the chlorine-containing organic solvents per se are harmful to the human body, and can generate a harmful gas, for example, phosgene or a hydrogen chloride gas by the occurrence of a fire. Also, recently, the chlorine-containing organic solvents have been designated as a pollutant of the global environment, in that they lead to a destruction of the ozonosphere.

In the conventional methods, such dangerous organic solvents are often used from the viewpoint of productivity, but improvements in the quality of the working environment and in safety are now considered more important than productivity.

Furthermore, the use of the organic solvent causes a deterioration in the quality of the resultant product, due to a small amount of residual solvent in the product. Accordingly, in view of the above-mentioned disadvantages, there is an urgent need for a new method of epoxidizing an olefin, without employing an organic solvent, by an in-situ method.

Still furthermore, a selectivity of reaction is highly contributory to a degree of separation between an oil phase and an aqueous phase in a washing step for a reaction product. When the selectivity of reaction is low, the resultant reaction product is emulsified in the washing step and this emulsification causes the reaction product to be useless. In other words, even if the reaction per se is carried out smoothly, if the reaction product cannot be smoothly separated from the reaction system by the washing procedure, this reaction process is considered incomplete.

SUMMARY OF THE INVENTION

Therefore, an object of the present invention is to provide a method of producing an olefin oxide by an in-situ epoxidizing reaction, without using an organic solvent.

Another object of the present invention is to provide a method of producing an olefin oxide at a high selectivity of the epoxidizing reaction, while restricting side reactions.

The above-mentioned objects can be attained by the method of the present invention, in which a specific side reaction-inhibiting agent is added to an epoxidizing reaction system.

The method of the present invention for producing an olefin oxide comprises the steps of:

epoxidizing an α-olefin having 6 to 30 carbon atoms per molecule thereof in an aqueous oxidant solution containing hydrogen peroxide, acetic acid, an acid catalyst consisting of at least one mineral acid and a side reaction inhibiting agent consisting of at least one water-soluble neutral salt in an amount of 2 to 30% based on the total weight of the aqueous oxidant solution, by an in-situ method, while maintaining the pH of the aqueous solution at a level of 0 to 1; and collecting the resultant reaction product from the epoxidizing system.

In the method of the present invention, the epoxidizing step can be carried out, without using an organic solvent, at a satisfactory productivity, but the method of the present invention does not restrict the employment of an organic solvent in the epoxidizing step.

DESCRIPTION OF THE PREFERRED EMBODIMENTS

The method of the present invention comprises a step of epoxidizing an α-olefin in an aqueous oxidant solution containing an oxidant mixture consisting of hydrogen peroxide with acetic acid, in the presence of an acid catalyst and in the presence of a specific side reaction-inhibiting agent, and a step of collecting the resultant reaction product.

In the epoxidizing step, the starting material is an α-olefin having 6 to 30 carbon atoms per molecule thereof having a double bond located at a terminal portion (α-position) of the molecular chain. The α-olefin is usually selected from 1-hexadecene, 1-octadecene, 1-tetradecene, 1-dodecene, 1-decene, 1-eicosene, 1-octene, and 1-hexene.

The oxidant mixture consists of hydrogen peroxide and acetic acid and generates peracetic acid that epoxidizes the olefin.

In the epoxidizing step, the hydrogen peroxide is preferably present in a molar ratio of from 0.5 to 3.5 to the olefin, and the acetic acid is present in a molar ratio of from 0.05 to 0.7 to the α-olefin.

The acetic acid is converted to peracetic acid, $CH_3COOOH$, by an in-situ reaction with hydrogen peroxide.

The hydrogen peroxide usable for the present invention is usually in the form of an aqueous solution thereof, in a concentration of 25 to 75% by weight, preferably 50 to 70% by weight.

The acid catalyst usable for the present invention comprises at least one mineral acid usable for a conventional in-situ method, preferably selected from sulfuric acid, nitric acid and perchloric acid.

A preferable mineral acid for the acid catalyst is sulfuric acid.

The acid catalyst is preferably present in an amount of from 0.2% to 30% based on the total weight of the hydrogen peroxide and acetic acid.

In the method of the present invention, the epoxidizing step for the α-olefin must be carried out not only in the presence of the acid catalyst but also in the presence of a side reaction-inhibiting agent consisting of at least one water-soluble neutral salt.

The water-soluble neutral salt for the side reaction-inhibiting agent is preferably selected from the group consisting of neutral salts of alkali metals with inorganic acids selected from the group consisting of sulfonic acid, nitric acid, perchloric acid, hydrochloric acid and chloric acid.

The alkali metals are preferably selected from the group consisting of sodium and potassium.

Preferably, the water-soluble neutral acids are selected from the group consisting of sodium sulfate, potassium sulfate, sodium nitrate, sodium perchlorate, and sodium chloride.

The side reaction-inhibiting agent is present in an amount of 2 to 30% based on the total weight of the aqueous oxidant solution containing hydrogen peroxide, acetic acid, the acid catalyst and the side reaction-inhibiting agent. If the amount of the side reaction-inhibiting agent is less than 2%, the resultant side reaction-inhibiting effect is unsatisfactory. Also, the amount of the side reaction-inhibiting agent of more than 30% is no longer contributory to enhancing the side reaction inhibiting effect and is therefore not economical.

Preferably, the amount of the side reaction-inhibiting agent is 15% to 30%, based on the total weight of the aqueous solution. More preferably, the side reaction-inhibiting agent is saturated in the aqueous solution.

The side reaction-inhibiting agent is preferably present in an equivalent weight of from 0.5 to 4.5, more preferably 1.8 to 2.2, per equivalent weight of the acid catalyst, in the aqueous oxidant solution.

The side reaction-inhibiting agent may be synthesized immediately before the start of the epoxidizing reaction, by adding an acid component and a base component of the salt to the reaction system.

In the epoxidizing step, the pH of the aqueous oxidant solution must be maintained at a level of 0 to 1. When the pH is lower than 0, the side reactions are undesirably enhanced. When the pH is higher than 1, the epoxidizing reaction rate is lowered and the reaction efficiency is decreased.

The epoxidizing step is preferably carried out at a temperature of from 50° C. to 90° C., more preferably 60° C. to 80° C., as employed in the conventional in-situ method.

In the in-situ epoxidizing method, the acid catalyst effectively promotes the generation of peracetic acid from hydrogen peroxide and acetic acid. Accordingly, only from the point of view of promoting the peracidgenerating reaction, it is considered that the production of the α-olefin oxide is promoted by raising the acidity of the acid catalyst. Nevertheless, the acid catalyst having a high acidity serves as a catalyst for undesirable side reactions, for example, a cleavage reaction of the epoxy ring structure and a polymerization reaction of the resultant olefin epoxide. Accordingly, to obtain the resultant α-olefin epoxide at a high yield, it is important to restrict these side reactions.

In the method of the present invention, it is assumed that the use of the water-soluble neutral salt in the specific amount will effectively control the acidity of the aqueous oxidant solution to a level at which the undesirable side reactions are restricted, without restricting the epoxidizing reaction of the α-olefin.

Also, the presence of the water-soluble neutral salt in an amount of 20% to 30% effectively decreases the concentration of the resultant α-olefin oxide in the aqueous phase of the reaction system so as to restrict the side reactions in the aqueous phase, and thus the side reactions in the whole reaction system can be restricted.

As mentioned above, the epoxidizing reaction of the α-olefin can be effected at a high selectivity without using an organic solvent.

Accordingly, the problems of the conventional in-situ epoxidizing method using an organic solvent harmful for the human body and polluting the global environment, and sometimes causing a fire, can be solved by the method of the present invention. Also, the product of the method of the present invention is free from the undesirable organic solvent, and thus has an improved quality.

In the method of the present invention, after the epoxidizing step is completed, the resultant reaction mixture is divided into an oil phase fraction comprising the epoxidizing product and an aqueous phase fraction. The target α-olefin epoxide can be collected from the oil phase fraction by a customary method.

EXAMPLES

The present invention will be further explained by the following examples.

EXAMPLES 1 to 7

In each of Examples 1 to 7, a reaction mixture consisting of 1.0 mole of the type of α-olefin as indicated in Table 1, 30 g (0.5 mole) of acetic acid, 7.84g of a 25% aqueous sulfuric acid solution (containing 1.96g of sulfuric acid), a neutral inorganic salt of the type as indicated in Table 1 and in an equivalent weight as indicated in Table 1, per equivalent weight of sulfuric acid and 68.03g of a 60% hydrogen peroxide aqueous solution (containing 1.2 moles of hydrogen peroxide) was charged in a reaction flask equipped with a stirrer, a thermometer and a condenser, and having a capacity of 500 ml. The reaction mixture was subjected to an epoxidizing reaction at a temperature of 70° C. for 12 hours while stirring at a rotation number of 300 rpm.

After the completion of the reaction, the resultant reaction mixture was allowed to divide into an oil phase fraction and an aqueous phase fraction, and the oil phase fraction separated from the aqueous phase fraction.

A portion of the oil phase fraction was subjected to a gas chromatographic analysis, to determine the yield of the aimed α-olefin epoxide, a residue of non-reacted α-olefin, an amount of a by-product consisting of 1,2-diol compounds, an amount of another by-product, and the selectivity of the epoxidization of the α-olefin. The analysis results are shown in Table 1.

The 1,2-diol compounds included alkane-1, 2-diols. The amount of another by-product was calculated from the following equation.

Amount of another by product (%) = 100 − (residue (%) of non-reacted olefin + yield (%) of the aimed olefin epoxide + amount (%) of the 1,2-diol compounds).

The selectivity of the epoxidization of the olefin is calculated from the following equation.

Selectivity of epoxidization of olefin (%) =

$$\frac{\text{yield (\%) of olefin epoxide}}{(100 - \text{residue (\%) of non-reacted olefin})}$$

Also, the pH of the aqueous phase fraction in the reaction mixture immediately after the start of the reaction procedure was measured and is indicated in Table 1.

Further, after the completion of the reaction procedure, the reaction mixture was washed twice each time with 200 ml of water, once with 200 ml of a 0.5% aqueous NaOH solution and then twice each time with 200 ml of water. After the washing procedures, the separation of the oil phase fraction and the aqueous phase fraction from each other was observed and evaluated as follows.

Class 3: Clearly separated
Class 2: Partially emulsified
Class 1: Completely emulsified The test results are shown in Table 1.

EXAMPLES 8 to 15

In each of Examples 8 to 15, the same procedures as in Example 1 were carried out except that the 7.8g of 25% aqueous sulfuric acid solution was replaced by 14.80g of a 50% aqueous sulfuric acid solution (containing 7.4g of sulfuric acid, and the type of the α-olefin, the type and equivalent weight of the neutral inorganic salt per equivalent weight of sulfuric acid, the content of the neutral inorganic salt in the aqueous phase fraction and the pH of the aqueous phase fraction in the reaction mixture were as indicated in Table 1.

The test results are shown in Table 1.

TABLE 1

| Example No. | Type of α-olefin | Neutral inorganic salt(*)1 Type | Neutral inorganic salt(*)1 Amount (*)2 | Content of neutral salt in aqueous phase fraction (%) | pH of aqueous phase fraction | Residue of non-reacted α-olefin (%) | Yield of α-olefin epoxide (%) | Amount of 1-2 diol compounds (%) | Amount of other by-product (%) | Selectivity of epoxydization of α-olefin (%) | Separation of aqueous phase fraction from oil phase fraction (class) |
|---|---|---|---|---|---|---|---|---|---|---|---|
| Example 1 | 1-Hexadecene | Na$_2$SO$_4$ | 3.5 | 8.58 | 0.3 | 16.45 | 79.43 | 0.65 | 3.47 | 95.07 | 3 |
| 2 | 1-Hexadecene | Na$_2$SO$_4$ | 2.0 | 5.09 | 0.2 | 11.92 | 85.52 | 0.86 | 1.70 | 97.09 | 3 |
| 3 | 1-Hexadecene | NaNO$_3$ | 2.0 | 3.11 | 0.2 | 11.58 | 86.34 | 0.87 | 1.21 | 97.65 | 3 |
| 4 | 1-Hexadecene | NaClO$_4$ | 2.0 | 4.42 | 0.2 | 11.99 | 86.17 | 0.85 | 0.99 | 97.91 | 3 |
| 5 | 1-Octadecene | Na$_2$SO$_4$ | 2.0 | 5.09 | 0.2 | 11.38 | 87.94 | 0.00 | 0.68 | 99.23 | 3 |
| 6 | 1-Eicosene | Na$_2$SO$_4$ | 2.0 | 5.09 | 0.2 | 12.35 | 87.05 | 0.00 | 0.60 | 99.31 | 3 |
| 7 | 1-Tetradecene | Na$_2$SO$_4$ | 2.0 | 5.09 | 0.2 | 10.02 | 87.29 | 1.02 | 1.67 | 97.01 | 3 |
| 8 | 1-Dodecene | Na$_2$SO$_4$ | 2.0 | 21.42 | 0.2 | 5.08 | 93.31 | 1.02 | 0.59 | 98.30 | 3 |
| 9 | 1-Decene | Na$_2$SO$_4$ | 2.0 | 21.42 | 0.2 | 4.78 | 93.04 | 1.32 | 0.86 | 97.71 | 3 |
| 10 | 1-Octene | Na$_2$SO$_4$ | 2.0 | 21.2 | 0.2 | 5.47 | 93.68 | 0.81 | 0.04 | 99.10 | 3 |
| 11 | 1-Octene | K$_2$SO$_4$ | 2.0 | 21.70 | 0.2 | 5.51 | 93.66 | 0.77 | 0.06 | 99.12 | 3 |
| 12 | 1-Octene | NaClO$_4$ | 2.0 | 16.29 | 0.2 | 5.14 | 93.99 | 0.84 | 0.03 | 99.08 | 3 |
| 13 | 1-Octene | NaNO$_3$ | 3.0 | 16.86 | 0.2 | 5.52 | 92.89 | 0.71 | 0.88 | 98.32 | 3 |
| 14 | 1-Hexene | Na$_2$SO$_4$ | 3.0 | 25.30 | 0.3 | 4.49 | 92.62 | 0.21 | 2.68 | 96.97 | 3 |

TABLE 1-continued

| Item | Reaction Mixture | | | | | Analysis Result | | | | | |
|---|---|---|---|---|---|---|---|---|---|---|---|
| | Type of α-olefin | Neutral inorganic salt(*)₁ | | Content of neutral salt in aqueous phase fraction (%) | pH of aqueous phase fraction | Residue of non-reacted α-olefin (%) | Yield of α-olefin epoxide (%) | Amount of 1-2 diol compounds (%) | Amount of other by-product (%) | Selectivity of epoxydization of α-olefin (%) | Separation of aqueous phase fraction from oil phase fraction (class) |
| Example No. | | Type | Amount (*)₂ | | | | | | | | |
| 15 | 1-Hexene | KClO₄ | 3.0 | 24.83 | 0.3 | 4.41 | 92.89 | 0.66 | 2.04 | 97.18 | 3 |

Note:
(*)₁Neutral inorganic salt = Side reaction-inhibiting agent
(*)₂Equivalent weight of salt per equivalent weight of acid catalyst

COMPARATIVE EXAMPLES 1 to 10

In each of Comparative Examples 1 to 10, the same procedures as in Example 1 were carried out except that the type of the α-olefin, the type and amount of the acid catalyst and the neutral inorganic salt, the content of the neutral inorganic salt in the aqueous phase fraction and the pH of the aqueous phase fraction were as indicated in Table 2.

The test results are shown in Table 2.

COMPARATIVE EXAMPLE 11

The same procedures as in Example 1 were carried out with the following exception.

The 1-hexadecene was replaced by 1.0 mole of 1-octene.

The acetic acid was replaced by 23g of a 98% aqueous formic acid (0.5 mole).

The sulfuric acid was not employed.

The anhydrous sodium sulfate was used in an amount of 12g (0.084 mole) together with 7.6g (0.11 mole) of sodium formiate.

The reaction temperature was 40° C.

The test results are as shown in Table 2.

In comparison of Table 1 to Table 2, it is clear that in accordance with the method of the present invention, α-olefins can be converted to corresponding α-olefin epoxides with a high epoxidization selectivity, even in the absence of an organic solvent, and that the resultant α-olefin epoxide has a high degree of purity.

We claim:

1. A method of producing an α-olefin oxide comprising the steps of:
    epoxidizing an α-olefin having 6 to 30 carbon atoms per molecule thereof in an aqueous oxidant solution containing hydrogen peroxide, acetic acid, an acid catalyst consisting of at least one mineral acid and a side reaction-inhibiting agent consisting of at least one water-soluble neutral salt in an amount of 2 to 30% based on the total weight of the aqueous oxidant solution, by an in-situ method, while maintaining the pH of the aqueous solution at a level of 0 to 1; and
    collecting the resultant reaction product from the epoxidizing system.

TABLE 2

| Item | | Reaction Mixture | | | | Analysis Result | | | | | |
|---|---|---|---|---|---|---|---|---|---|---|---|
| | Type of α-olefin | Neutral inorganic salt(*)₁ | | Content of neutral salt in aqueous phase fraction (%) | pH of aqueous phase fraction | Residue of non-reacted α-olefin (%) | Yield of α-olefin epoxide (%) | Amount of 1-2 diol compounds (%) | Amount of other by-product (%) | Selectivity of epoxydization of α-olefin (%) | Separation of aqueous phase fraction from oil phase fraction (class) |
| Example No. | | Type | Amount (*)₂ | | | | | | | | |
| Comparative Example 1 | 1-Hexadecene | DBS(*)₃ | 5.00 g | — | 0.2 | 0.87 | 24.78 | 41.88 | 32.47 | 24.99 | 1 |
| 2 | 1-Hexadecene | — | — | — | less than 0 | 7.30 | 76.64 | 4.31 | 19.05 | 82.67 | 1 |
| 3 | 1-Hexadecene | Pyrophosphic acid(*)₄ | 1.96 g | — | less than 0 | 11.85 | 58.54 | 12.11 | 17.50 | 66.41 | 1 |
| 4 | 1-Tetradecene | — | — | — | less than 0 | 8.76 | 69.82 | 8.69 | 12.73 | 76.52 | 1 |
| 5 | 1-Dodecene | — | — | — | less than 0 | 7.51 | 67.99 | 10.21 | 14.29 | 73.51 | 1 |
| 6 | 1-Octene | — | — | — | less than 0 | 26.59 | 2.14 | 24.85 | 46.42 | 2.92 | 1 |
| 7 | 1-Hexene | — | — | — | less than 0 | 21.87 | 0.54 | 31.56 | 46.03 | 0.69 | 1 |
| 8 | 1-Octene | DBS(*)₃ | 5.00 g | — | 0.2 | 0.41 | 1.45 | 44.58 | 53.56 | 1.46 | 1 |
| 9 | 1-Octene | Phosphic acid(*)₄ | 5.00 g | — | less than 0 | 32.87 | 46.89 | 18.75 | 1.49 | 69.85 | 1 |
| 10 | 1-Octene | NaHSO₄ (*)₃ | 1.00 g | 0.94 | less than 0 | 25.47 | 58.71 | 13.45 | 2.37 | 78.77 | 1 |
| 11 | 1-Octene | (*)₅ | — | 17.72 | 2.5 | 65.14 | 27.61 | 3.42 | 3.83 | 79.20 | 3 |

Note:
(*)₃Sodium dodecylbenzenesulfonate used in place of sulfuric acid
(*)₄Used in place of sulfuric acid
(*)₅A mixture of 0.084 mole of anhydrous sodium sulfate with 0.11 mole of sodium formate 2. The method as claimed in claim 1, wherein the hydrogen peroxide is present in a molar ratio of from 0.5 to 3.5 to the α-olefin.

3. The method as claimed in claim 1, wherein the acetic acid is present in a molar ratio of from 0.05 to 0.7 to the α-olefin.

4. The method as claimed in claim 1, wherein the mineral acid for the acid catalyst is selected from the group consisting of sulfuric acid, nitric acid, and perchloric acid.

5. The method as claimed in claim 1, wherein the acid catalyst is present in an amount of from 0.2% to 30% based on the total weight of the hydrogen peroxide and acetic acid.

6. The method as claimed in claim 1, wherein the water-soluble neutral salt for the side reaction-inhibiting agent is selected from the group consisting of neutral salts of alkali metals with inorganic acids selected from the group consisting of sulfuric acid, nitric acid, perchloric acid, hydrochloric acid and chloric acid.

7. The method as claimed in claim 1, wherein the water-soluble neutral salt for the side reaction-inhibiting agent is selected from the group consisting of sodium sulfate, potassium sulfate, sodium nitrate, sodium perchlorate, and sodium chloride.

8. The method as claimed in claim 1, wherein the side reaction-inhibiting agent is present in an equivalent weight of from 0.5 to 4.5, per equivalent weight of the acid catalyst.

9. The method as claimed in claim 1, wherein the o epoxidizing step is carried out at a temperature of 50° C. to 90° C.

10. The method as claimed in claim 1, wherein the side reaction-inhibiting agent is saturated in the aqueous oxidant solution.

* * * * *